(12) United States Patent
Ranganathan et al.

(10) Patent No.: US 6,706,263 B2
(45) Date of Patent: Mar. 16, 2004

(54) COMPOSITION FOR ALLEVIATING SYMPTOMS OF UREMIA IN PATIENTS

(75) Inventors: Natarajan Ranganathan, Broomall, PA (US); Jack Dickstein, Huntingdon Valley, PA (US)

(73) Assignee: Kibow Biotech Inc., Philadelphia, PA (US)

( * ) Notice: Subject to any disclaimer, the term of this patent is extended or adjusted under 35 U.S.C. 154(b) by 5 days.

(21) Appl. No.: 09/557,011

(22) Filed: Apr. 20, 2000

(65) Prior Publication Data

US 2001/0051150 A1 Dec. 13, 2001

Related U.S. Application Data

(60) Provisional application No. 60/131,774, filed on Apr. 30, 1999.

(51) Int. Cl.$^7$ .................. A01N 63/00; A61K 31/00; A61K 9/50; A61K 9/48; A61K 47/00
(52) U.S. Cl. .................. 424/93.4; 424/195.18; 424/457; 424/463; 424/490; 424/500; 514/780; 514/786; 435/252.1
(58) Field of Search .................. 424/725, 776, 424/4, 51, 457, 93–1, 93.4, 195.18, 490, 500, 463; 514/780, 778; 435/262.5, 267, 268, 252.1

(56) References Cited

PUBLICATIONS

Yatzidis et al. Newer Oral Sorbents in Uremia; Clinical Nephrology, vol. 11, No. 2, pp. 105–106, 1979.*
Prakash et al. Preparation and Invitro Analysis of Microencapsulated Genetically Engineered E. coli DH5 Cells for Urea and Ammonia Removal; Biotechnology and Bioengineering, vol. 46, pp. 621–626, 1995.*
Goldenhersh et al. Effect of Microencapsulation on Competitive Adsorption in Intestinal Fluids; Kidney International, vol. 10 p. S–251–S–253, 1976.*
Bliss et al., "Supplementation with gum arabic fiber increases fecal nitrogen excretion and lowers serum urea nitrogen concentration in chronic renal failure patients consuming a low–protein diet $^{1-4}$", *Am. J. Clin. Nutr.* 1996 63:392–398.
Chang, T.M.S., "*Artificial Cells*", Chapter 5, in *Biomedical Applications of Microencapsulation*, edited by Lim, F. CRC Press Florida, pp 86–100.
Clark et al., "Perfusion of Isolated Intestinal Loops in the Management of Chronic Renal Failure", *Trans. Am. Soc. Artif. Intrn. Organs* 1962 8:246–251.
Dunn et al., "Gas Chromatographic Determination of Free Mono–, Di–, and Trimethylamines in Biological Fluids", *Analytical Chemistry* 1976 48:41–44.
Einbacher and Carter, "The Role of the Microbial Flora in uremia", *J. Exp. Med.* 1966 123:239–250.
Friedman et al., "Hypertrigylceridemia Responsive to Charcoal Sorption", *Proc. Clin. Dia. Trans. Forum* 1977 7:183–184.
Goldenhersh et al., "Effect of microencapsulation on competitive adsorption in intestinal fluids", *Kidney Int.* 1976 10:S251–S253.
Gotch et al., "Theoretical Considerations on Molecular Transport in Dialysis and Sorbent Therapy for Uremia", *Journal of Dialysis* 1976–1977 1(2) :105–144.
Kjellstrand et al., "On the Clinical use of Microencapsulated Zirconium Phosphate–Urease for the Treatment of Chronic Uremia", *Trans. Am. Soc. Artif. Intern. Organs* 1981 27:24–29.

* cited by examiner

*Primary Examiner*—Patricia Patten
(74) *Attorney, Agent, or Firm*—Licata & Tyrrell P.C.

(57) ABSTRACT

Microencapsulated and/or enteric coated compositions containing a mixture of sorbents with specific adsorption affinities for uremic toxins including ammonia, urea, creatinine, phenols, indoles, and middle molecular weight molecules and a bacterial source which metabolizes urea and ammonia are provided. Also provided are methods of using these compositions to alleviate symptoms of uremia in patients.

4 Claims, No Drawings

COMPOSITION FOR ALLEVIATING SYMPTOMS OF UREMIA IN PATIENTS

This application claims the benefit of provisional U.S. Application Ser. No. 60/131,774, filed Apr. 30, 1999.

BACKGROUND OF THE INVENTION

Kidney disease is ranked fourth among the major diseases in the United States afflicting over 20 million Americans. More than 90,000 patients die each year because of kidney diseases. In recent years the number of chronic kidney failure patients has increased about 11 percent annually. About 80,000 Americans on dialysis die of various complications each year and more than 27,000 are on waiting lists for kidney transplants each year with only about 11,000 of these patients receiving transplants.

Nearly 250,000 Americans suffer from end stage renal disease (ESRD), which is the final stage in chronic renal failure. Currently hemo- or peritoneal-dialysis and renal transplant are the only treatment modalities. However, the economic costs of these treatment modalities is extremely high. For example, in 1996 in the United States alone, the annual cost of ESRD treatment was over 14 billion dollars. In developing and underdeveloped countries with low health care budgets, ESRD patients are deprived access to such treatments due to their high costs. Accordingly, there is a need for alternative modalities of treatment for uremia.

A number of treatment attempts have been based on the use of the bowel as a substitute for kidney function. During a normal digestive process the gastrointestinal tract delivers nutrients and water to the bloodstream and eliminates waste products and undigested materials through the bowel. The intestinal wall regulates absorption of nutrients, electrolytes, water and certain digestive aiding substances such as bile acids. The intestinal wall also acts as a semipermeable membrane allowing small molecules to pass from the intestinal tract into the bloodstream and preventing larger molecules from entering the circulation.

Nitrogenous wastes such as urea, creatinine and uric acid, along with several other small and medium molecular weight compounds, flow into the small intestine and equilibrate across the small intestine epithelium. Studies of intestinal dialysis have shown a daily flow of 71 grams of urea, 2.9 grams of creatinine, 2.5 grams of uric acid and 2.0 grams of phosphate into the intestinal fluid (Sparks, R. E. *Kidney Int. Suppl.* 1975 Suppl 3, 7:373 376). Accordingly, various invasive and noninvasive attempts including external gut fistula, intestinal dialysis, induced diarrhea, and administration of oral sorbents and/or encapsulated urease enzyme have been made to extract uremic waste from the gastrointestinal tract (Twiss, E. E. and Kolff, W. J. *JAMA* 1951 146:1019–1022; Clark et al. *Trans. Am. Soc. Artif. Intrn. Organs* 1962 8:246–251; Pateras et al. *Trans. Am. Soc. Artif. Intrn. Organs* 1965 11:292–295; Shimizu et al. *Chemical Abstracts* 1955 103:129004; Kjellstrand et al. *Trans. Am. Soc. Artif. Intern. Organs* 1981 27:24–29; and Kolff, W. J. *Kidney Int.* 1976 10:S211–S214).

Activated charcoal was the first oral sorbent studied for treatment of uremia. Activated charcoal is a highly porous material with large surface area obtained by carbonization of organic materials such as wood, petroleum, coal, peat, and coconut shell followed by activation with steam, carbon dioxide or chemicals such as zinc chloride. Solute adsorption by activated charcoal depends on a number of factors including concentration of the solute in bulk phase, chemical nature of the solute, temperature, and pH. In general, however, activated charcoal binds more avidly to non-polar solutes than polar solutes. In in vivo studies, 190 grams of activated charcoal was required to remove 450 mg of creatinine (Goldenhersh et al. *Kidney Int.* 1976 10:S251–S253). This reduced efficacy is believed to be due to adsorption of other lipophilic compounds such as cholesterol and related bile acids (Kolff, W. J. *Kidney Int.* 1976 10:S211–S214; Goldenhersh et al. *Kidney Int.* 1976 10:S251–S253). Microencapsulation of activated charcoal has been shown to reduce the amount of charcoal needed to 50 grams (Goldenhersh et al. *Kidney Int.* 1976 10:S251–S253).

AST-120, a proprietary and specially-prepared, coated material of porous carbon of 0.2 to 0.4 mm, has been demonstrated to be a more effective charcoal based adsorbent. A dose of 3.2 to 7.2 grams to uremic patients has been disclosed to delay the rise in serum level of creatinine and delay the onset of renal dysfunction in nephrectomized rats as well as 27 uremic patients (Owadu, A. and Shiigai, T. *Am. J. Nephrol.* 1996 16(2):124–7; and Okada, K. and Takahashi, S. *Nephrol. Dial. Transplant.* 1995 10(5):671–6).

Several studies have also shown that ingestion of dialdehyde starch, also referred to as oxystarch, resulted in increased excretion of non-protein nitrogen (Giordano et al. *Bull. Soc. Ital. Biol. Sper.* 1968 44:2232–2234; Giordano et al. *Kidney Int.* 1976 10:S266–S268: Friedman et al. *Proc. Clin. Dia. Trans. Forum* 1977 7:183–184). Unlike activated charcoal where adsorption of the uremic solute is a physical process easily reversible, dialdehyde starch binds urea and ammonia via chemisorption involving covalent binding to the two-aldehyde groups. However, like activated charcoal, ingestion of very large amounts of about 30–50 grams only removed 1.5 grams of urea. Additional studies wherein dialdehyde starch and activated charcoal were both ingested demonstrated some improvement in uremic waste removal (Friedman et al. *Proc. Clin. Dia. Trans. Forum* 1977 7:183–184). Further, coating of dialdehyde starch with gelatin and albumin resulted in 6-fold better sorbency as compared to uncoated dialdehyde starch (Shimizu et al. *Chemical Abstracts* 1982 97:222903). More recently, retardation of progression of chronic renal failure has been shown following administration of chitosan coated oxycellulose or cellulose dialdehyde (Nagano et al. Medline Abstract UI 96058336 1995).

Locust bean gum, a naturally available carbohydrate based polymeric oral sorbent, when administered at 25 grams/day in cottonseed oil to uremic patients, was also demonstrated to remove significant amounts of urea, creatinine and phosphate. Further, locust bean gum adsorbs about 10 times its own weight in water (Yatzidis et al. *Clinical Nephrology* 1979 11:105–106).

Dietary supplementation with gum arabic fiber has also been demonstrated to increase fecal nitrogen excretion and lower serum nitrogen concentration in chronic renal failure patients on low protein diets (Bliss et al. *Am. J. Clin. Nutr.* 1996 63:392–98).

Encapsulated urease enzyme has also been investigated as a nonabsorbable oral sorbent for binding ammonia. In early studies zirconium phosphate and encapsulated urease enzyme were used as a non-absorbable oral sorbent for binding ammonia (Kjellstrand et al. *Trans. Am. Soc. Artif. Intern. Organs* 1981 27:24–29). A liquid-membrane capsule device with encapsulated urease to hydrolyze urea to ammonia and citric acid to neutralize the ammonia has also been investigated (Asher et al. *Kidney Int.* 1976 10:S254–S258). Soil bacteria has also been used to recycle urea as metabolically useful amino acids (Setala, K. *Kidney Int. Suppl.* 1978 8:S194–202). In addition, genetically engineered *E. herbicola* cells have been encapsulated and demonstrated to convert ammonia into usable amino acids for the cells before being eliminated via the bowel. Microencapsulated genetically engineered *E. coli* DH5 cells have also been shown to be effective in removal of urea and ammonia in an in vitro system and in a uremic rat animal model (Prakash, S. and Chang, T. M. S. *Biotechnology* and *Bioengineering* 1995 46:621–26; and Prakash, S. and Chang, T. M. S. *Nature Med.* 1996 2:883–887).

For effective treatment of renal failure, however, it has been estimated that at least 6.0 grams of urea, 0.5 grams of creatinine, 0.5 grams of uric acid and 1.2 grams of phosphate must be removed. Accordingly, there is a need for more effective treatments which remove multiple uremic toxins at higher concentrations to alleviate the symptoms of uremia in patients.

The present invention relates to compositions and methods of using these compositions to alleviate the symptoms of uremia. Compositions of the present invention comprise a mixture of sorbents with specific adsorption affinities for uremic toxins such as ammonia, urea, creatinine, phenols, indoles, and middle molecular weight molecules. These compositions also comprise a bacterial source which metabolizes urea and ammonia. These compositions are microencapsulated and/or enteric coated to deliver the sorbent and bacterial source to the ileal and colonic regions wherein maximal resorption of uremic solutes and other molecules occurs.

SUMMARY OF THE INVENTION

An object of the present invention is to provide microencapsulated and/or enteric coated compositions which comprise a mixture of sorbents with specific adsorption affinities for uremic toxins including ammonia, urea, creatinine, phenols, indoles, and middle molecular weight molecules; and a bacterial source which metabolizes urea and ammonia for use in patients in the alleviation of symptoms associated with uremia.

Another object of the present invention is to provide a method of alleviating symptoms of uremia in a patient which comprises administering orally to a patient suffering from uremia a microencapsulated and/or enteric coated composition comprising a mixture of sorbents with specific adsorption affinities for uremic toxins including ammonia, urea, creatinine, phenols, indoles, and middle molecules; and a bacterial source which metabolizes urea and ammonia.

DETAILED DESCRIPTION OF THE INVENTION

In kidney failure there is a decrease in the glomerular filtration rate and the kidneys are unable to maintain homeostasis of the blood. Homeostatic balance of water, sodium, potassium, calcium and other salts is no longer possible and nitrogenous wastes are not excreted. Retention of water causes edema and as the concentration of hydrogen ions increases, acidosis develops. Nitrogenous wastes accumulate and a condition referred to as uremia develops in the blood and tissue. Uremic toxins can be defined as solutes that: (I) are normally excreted by healthy kidneys, (ii) accumulate progressively during the development of renal failure so that their concentration increases, and (iii) inhibit various physiologic and biochemical functions; as a whole, they contribute to a complex set of clinical symptoms that comprise the Uremic Syndrome. Examples of uremic toxins include, but are not limited to, ammonia, urea, creatinine, phenols, indoles, and middle molecular weight molecules. More specifically, in uremia, the concentration of serum creatinine, blood urea nitrogen (BUN), uric acid, and guanidino compounds such as N-methyl guanidine (NMG) and guanidino succinic acid (GSA) are significantly altered with accompanying abnormalities in acid-base equilibrium, electrolytes and water retention. In addition, there are several known and unknown substances of low and middle molecular weight which have been identified as uremic toxins which also accumulate. If untreated the acidosis and uremia can cause coma and eventually death.

Further, as a result of poor clearance of waste products of metabolism, there are some compensatory as well as adaptive processes, which further complicate the condition. For example, bacterial overgrowth of the normal flora of the gut occurs when kidney function is reduced to less than 20% and creatinine levels in the serum increase to 8 mg/dl. Substantially increased metabolism of normal substrates and a large variety of toxic amines, such as methylamine, dimethylamine, trimethylamine, phenols and indole metabolites also occurs from this bacterial outgrowth. When the small gut bacterial growth increases, there is an increase in ammonia release which then enters the enterohepatic circulation and is converted to urea.

The introduction of renal dialysis has contributed to rapid progress in the clinical treatment of renal failure and elucidation of uremia. When a patient has mild kidney failure where the serum creatinine level is less than 400 $\mu$mol/L, the patient does not require renal replacement therapy such as dialysis or renal transplant. However, in general, when the serum creatinine level rises to 900 $\mu$mol/L, the patient needs routine dialysis or a kidney transplant to survive.

Dialysis can serve as a lifetime therapy for ESRD patients. Phosphate binders such as calcium acetate, calcium carbonate or aluminum hydroxide are generally prescribed for uremic patients receiving dialysis to reduce elevated phosphate levels. In general, however, dialysis is very expensive, inconvenient, time consuming and may occasionally produce one or more side effects. With a successful kidney transplant, a patient can live a more normal life with less long-term expense. However, there are also high costs associated with transplant surgery, the recovery period and the continuous need for antirejection medications. Further, there is oftentimes a shortage of suitable donors. Accordingly there is a need for alternative strategies.

In the present invention, compositions are provided which comprise a mixture of sorbents selected for their specific adsorption affinities for uremic toxins such as ammonia, urea, creatinine, phenols, indoles, and middle molecular weight molecules. For example, in a preferred embodiment, the mixture of sorbents comprises: oxystarch or oxycellulose with a specific adsorption affinity for urea and ammonia; locust bean gum with a specific adsorption affinity for creatinine and urea; and activated charcoal with a specific adsorption affinity for creatinine guanidines, phenol, Indican and middle molecular weight undefined components. Compositions of the present invention further comprise a bacterial source which metabolizes urea and ammonia, preferably to amino acids which can be used by the bacteria or the patient. Examples of bacterial sources useful in the present invention include, but are not limited, *E. coli* DH5, *Sprosarcina urae* and genetically modified yeast cells such as *S. pombe*. The composition is then enteric coated and/or microencapsulated. Enteric coating of the composition is specifically designed to deliver the sorbents and bacterial source at the ileal and colonic regions of the bowel where maximal resorption of uremic solutes and other molecules are found to occur. This is preferably achieved via an enteric coating material which disintegrates and dissolves at a pH of 7.5 or higher. Examples of enteric coatings with these characteristics include, but are not limited to, Zein, polyglycolactic acid, polylactic acid, polylactide-coglycolide and similar coating materials. Enteric coatings also enable delivery of the sorbents to their site of action in relatively native form without binding of various digestive materials to the sorbents prior to reaching the target region. Alternatively, or in addition, the compositions of the present invention can be microencapsulated thus permitting the compositions to perform like microscopic dialysis units as described by Chang, T. M. S. (Artificial Cells, Chapter 5, in Biomedical Applications of Microencapsulation, edited by Lim, F. CRC Press Fla., pp 86–100). In this embodiment, the composition is coated with a non-absorbable polymeric compound which permits only small and middle-sized molecules into the core wherein the mixture of solvent and bacterial source are located. Examples of non-absorbable polymeric coatings for microencapsulation include, but are not limited to, alginate/alginic acid, chitosan, cellulose acetate pthalate, hydroxyethyl cellulose and similar coating materials. Microencapsulation prevents the binding of macromolecules and other digestive materials which substantially reduce the efficacy of the sorbents to specifically adsorb the uremic solutes to the sorbents of the mixture. The microcapsules pass through the bowel, with the mixture of sorbents adsorbing multiple uremic solutes and the bacterial source metabolizing urea and ammonia and urea, and are then excreted intact from the bowel. Thus, in this embodiment, the patient is protected from the possibility of microbial infection by the bacterial source as the bacterial source is kept within the microcapsule. Accordingly, in a preferred embodiment, compositions of the present invention are both microencapsulated and enteric coated.

Compositions of the present invention may further comprise a phosphate binding agent such as aluminium hydroxide, calcium carbonate or calcium acetate and a water binding agent such as psyllium fibers, naturally occurring gums or modified starches.

Compositions of the present invention are administered orally to patients with uremia to alleviate the symptoms of uremia. By "alleviation of symptoms" of uremia, it is meant that the composition removes sufficient levels of uremic toxins such that a patient suffering from uremia either does not require dialysis, requires dialysis less frequently or for shorter durations, or does not require initiation of dialysis as soon.

In a preferred embodiment, oral delivery of the mixture of sorbents in the composition will be accomplished via a 2 to 4 ounce emulsion or paste mixed with an easy to eat food such as a milk shake or yogurt. The microencapsulated bacterial source can be administered along with the mixture of sorbents in the emulsion or paste or separately in a swallowable gelatin capsule.

A mathematical model of solute transport of oral sorbents has been developed based on the diffusion controlled solute flux into the intestinal lumen followed by physical binding or chemical trapping (Gotch et al. *Journal of Dialysis* 1976–1977 1(2):105–144). This model provides the theoretical basis of solute removal through the gut.

For example, gut clearance of urea is 10 to 12 ml/minute in normal renal function and is reduced to 3 to 4 ml/minute in patients with severely reduced renal function. This reduction in the clearance rate is independent of blood urea concentration and directly related to impaired renal function. The normal creatinine clearance rate is 2 to 5 ml/minute.

Further, at steady state, as rate of mass generation is equal to rate of mass elimination, the first order sorbent promoted gut clearance of any solute is given by the mass balance equation:

$$G_s = (K_r + K_g) C_s,$$

where $G_s$=rate of solute generated, $K_r$=rate of renal clearance, $K_g$=rate of gut clearance and $C_s$ is concentration of solute.

The process of sorbent binding, for a given amount of sorbent, is saturable. Thus, below the saturation levels, as the rate of gut clearance of the solute is first order, the above equation can be depicted as:

$$C_s = G_s / (K_r + K_g).$$

Above the saturation levels, as the rate of gut clearance is zero, the equation can be rewritten as:

$$C_s = (G_s - \text{sorbent capacity}) / K_r.$$

These equations are useful in predicting the efficacy of solute removal from the gut based in vitro studies.

In fact, this model was applied to Friedman's data on urea elimination by the gut in uremic patients using oxystarch oral sorbent (Friedman et al. *Trans. Am. Soc. Artif. Intern. Organs* 1974 20:161–167). With these data, the model showed that maximum sorbent capacity for native oxystarch oral sorbent was 1.5 g/day which is insufficient to replace dialysis or reduce the frequency of dialysis. This model also predicted that for the same patient data, at a protein catabolic rate of 0.95 grams/kg/24 hours and a urea generation of 5 mg/minute, the maximum sorbent capacity of oxystarch should be 7.2 grams of urea nitrogen/day and the gut clearance rate should be 5.6 ml/minute. Sorbent capacity lower than this, such as 5.4 grams of urea/day will at best delay dialysis by months provided the protein catabolic rate can be held at 0.6 grams/kg/24 hours. Thus, this model is useful in determining optimal results for various formulations of compositions of the present invention to alleviate symptoms of uremia in patients.

The following nonlimiting examples are provided to further illustrate the present invention.

EXAMPLES

Example 1

Source of Sorbents

Oxystarch (dialdehyde starch) was purchased from MPD-Labs, Feasterville, Pa. This is a pharmaceutical grade material (98% pure) with a moisture content of 13% and possessing a minimum 90% oxidized material as per the certificate of analysis by the supplier.

Locust bean gum (minimum 99% pure) was purchased from Sigma-Aldrich, St. Louis, Mo.

Activated charcoal, Supra A, pharmaceutical grade (99.9% purity) was purchased from Norit Corporation of America, Atlanta, Ga.

Each sorbent material was enteric coated with Zein; microencapsulated with ethocel; and microencapsulated with ethocel and then enteric coated with Zein as the shell materials. Encapsulation runs were performed using a disk process. Three separate shell material solutions were prepared: ethocel alone, Zein alone, and Zein in combination with ethocel. After the shell materials were prepared, each sorbent was added to the shell solution (to provide 60% theoretical payload) and mixed to form a dispersion. The dispersion was then sonicated and pumped at approximately 50 grams/minute onto a disk rotating at approximately 20,000 RPM to create microspheres. The microspheres were formed in a heated cone with an inside temperature of approximately 50° C. to evaporate the ethanol and water. The capsules were collected via a cyclone. The native particle size and the particle size after various encapsulations of these sorbents are depicted in Table 1.

TABLE 1

Encapsulation Formulations

| Run Number | Sample Number | Sorbent | Shell System | Initial Particle Size (μm) | Encapsulated Particle Size (μm) |
|---|---|---|---|---|---|
| 1 | 19-011 | Dialdehyde Starch | 10% Ethocel 90% Ethanol | Average: 20 | 10–100 Average: 60 |
| 2 | 19-012 | Dialdehyde Starch | 15% Zein 76% Ethanol 9% Water | Average: 20 | 5–80 Average: 30 |
| 3 | 19-013 | Dialdehyde Starch | 7.7% Zein 4.9% Ethocel 83% Ethanol 4.4% Water | Average: 20 | 10–100 Average: 50 |
| 4 | 19-014 | Locust Bean Gum | 10% Ethocel 90% Ethanol | Average: 100 | 10–120 Average: 50 |
| 5 | 19-015 | Locust Bean Gum | 15% Zein 76% Ethanol 9% Water | Average: 100 | 10–200 Average: 30 |
| 6 | 19-016 | Locust Bean Gum | 12.3% Zein 8% Ethocel 68% Ethanol 11.7% Water | Average: 100 | 30–200 Average: 70 |
| 7 | 19-017 | Activated Charcoal | 10% Ethocel 90% Ethanol | Average: 5 | 20–200 Average: 50 |
| 8 | 19-018 | Activated Charcoal | 15% Zein 76% Ethanol 9% Water | Average: 5 | 20–200 Average: 50 |
| 9 | 19-019 | Activated Charcoal | 12.3% Zein 8% Ethocel 68% Ethanol 11.7% Water | Average: 5 | 20–200 Average: 50 |
| 10 | 19-020 | Aluminium Hydroxide | 10% Ethocel 90% Ethanol | Average: 20 | 10–100 Average: 75 |
| 11 | 19-021 | Aluminium Hydroxide | 15% Zein 76% Ethanol 9% Water | Average: 20 | 10–500 Average: 300 needle-like |
| 12 | 19-022 | Aluminium Hydroxide | 12.3% Zein 8% Ethocel 68% Ethanol 11.7% Water | Average: 20 | 10–100 Average: 75 |
| 13 | 19-023 | Aluminium Hydroxide | 12% Zein 79% Ethanol 9% Water | Average: 20 | 10–100 Average: 50 | scanning electron micrographs (SEMs) of the raw materials including dialdehyde starch, locust bean gum, activated charcoal and aluminium hydroxide and the twelve microencapsulation formulations were also prepared. Run 11, produced rod-like capsules which was caused by the material not being fed directly into the center of the disk or by the solids content being too high. Run 11 was thus repeated as run 13 with the Zein decreased from 15% to 12% and was successful.

In addition to the SEMs of each run, digital photomicrographs were also taken.

Example 2
*E. coli* DH5 Cells

Genetically engineered *E. coli* DH5 cells are obtained from Organica Inc. Valley Forge, Pa. The cells are seed cultured, grown, harvested and microencapsulated in accordance with procedures described by Chang and Prakash (*Biotechnology and Bioengineering* 1995 46:621–26).

Example 3
Formulations

Relative in vitro efficacy of oxystarch, locust bean gum and activated charcoal in native (N), enteric coated (E), microencapsulated (M), and microencapsulated with enteric coating (ME) alone and in various combinations as shown in Table 2 is assessed.

TABLE 2

Sorbent Efficacy Determinations

| Formulation Number | Amount of Oxystarch (g) | Amount of Locust Bean Gum (g) | Amount of Activated Charcoal (g) |
|---|---|---|---|
| 1 | 0 | 0 | 15 |
| 2 | 0 | 5 | 10 |
| 3 | 0 | 10 | 5 |
| 4 | 0 | 15 | 0 |
| 5 | 5 | 0 | 10 |
| 6 | 5 | 5 | 5 |
| 7 | 5 | 10 | 0 |
| 8 | 10 | 0 | 5 |
| 9 | 10 | 5 | 0 |
| 10 | 15 | 0 | 0 |

As shown in Table 2, a three level three variable factorial formulation design is used with the constraint that sum total of the ingredients is constant at 15 grams. This design permits evaluation of individual sorbents (formulation numbers 1, 4 and 10), binary combinations (formulation numbers 2, 3, 6, 7, 8 and 9) and a single ternary 1:1:1 combination of sorbents (formulation number 5).

The efficacy of various concentrations of *E. coli* DH5 cells (5, 10 and 15 grams) in native form and APA (alginic acid-polyglycolide-alginate) microencapsulated form is then assessed.

Efficacy determinations are also made on formulations as depicted in Table 3 containing both sorbents and *E. coli* DH5.

TABLE 3

Formulation of sorbents plus *E. coli* DH5 efficacy determinations

| Formulation Number | Oxystarch (g) | Locust Bean Gum (g) | Activated Charcoal (g) | APA *E. coli* DH5 cells (g) |
|---|---|---|---|---|
| 1 | 5 | 5 | 5 | 5 |
| 2 | 5 | 5 | 5 | 10 |
| 3 | 5 | 5 | 5 | 15 |
| 4 | 5 | 5 | 10 | 5 |
| 5 | 5 | 5 | 15 | 5 |
| 6 | 5 | 10 | 5 | 5 |
| 7 | 5 | 15 | 5 | 5 |
| 8 | 10 | 5 | 5 | 5 |
| 9 | 15 | 5 | 5 | 5 |

As shown in Table 3, a three level four variable factorial design is used to evaluate the addition of APA-microencapsulated *E. coli* DH5 cells with constraints that the amount of each ingredient not exceed 15 grams and the maximum amount of the total formulation not exceed 25 grams.

From the experimental observations and determinations of Table 2, only those specific modified forms demonstrating highest sorbent efficacy both independently and in binary combination will be used in these formulations studies with APA microencapsulated *E. coli* DH5 cells.

A sorbent coating (E, M or ME) will then be selected for ternary sorbent formulation and integration with microencapsulated *E. coli* DH5 cells.

Example 4
In vitro Efficacy Evaluations

A simulated gastric fluid composed of NaCl, HCl and pepsin in distilled water and adjusted to pH 1.2 is prepared according to U.S. Pharmacopeia procedures for stability testing of formulations under acidic pH and gastric conditions. Every modified sorbent material, and binary and ternary formulation is tested by stirring a quantity of approximately 5 grams into a test solution of simulated gastric juice at 37° C. for 1 to 2 hours to ascertain the integrity of the modified sorbent.

A simulated synthetic intestinal fluid, composed of monobasic potassium hydrogen phosphate, sodium hydroxide, pancreatin mix and distilled water, is also prepared and adjusted to pH 7.5 according to the test solution preparations in U.S. Pharmacopeia. The intestinal fluid is fortified with uremic solutes to make a solution of 150 milligrams of urea, 30 milligrams of creatinine, and 30 milligrams of uric acid per 100 milliliters of synthetic intestinal fluid.

To vary the concentrations, this stock solution is diluted with non-fortified intestinal stock solution to make 75% and 50% concentrations of variable uremic intestinal fluid solutions. Initially 100%, 75% and 50% concentration uremic intestinal fluid solutions are evaluated with a 15 gram sorbent formulation containing S grams each of oxystarch, locust bean gum and activated charcoal. From these data, various experimental parameters including, but not limited to volume, concentration of uremic intestinal fluid, and time of pre- and post-treatment can be optimized. Optimal parameters are then used for all additional sorbent evaluations, formulations and experimental determinations. All experimental observations are made in triplicate.

However, initially, sorbent/formulation test runs of 5, 10 or 15 grams of sorbent or formulation are treated with 500 ml of fortified intestinal fluid of different concentrations in a graduated measuring cylinder and gently shaken for 8 hours. Samples are drawn from the supernatant at one hour intervals, centrifuged if necessary, and analyzed for urea creatinine and uric acid via commercially available kits (Sigma Diagnostics Company, St. Louis, Mo.). Once the adsorption capacity and equilibration times are determined, this period, estimated to be at least 2 hours, will be used.

All formulations shown in the Tables will then be tested. In these tests, 1.5 grams of sorbent formulation is treated with 50 ml of fortified intestinal fluid in a graduated measuring cylinder. The suspension is gently shaken. A sample is withdrawn every hour and analyzed for urea, creatinine and uric acid. The sediment volume is measured for all time intervals and used to determine the water absorbing capacity of each formulation. A plot of the time versus the amount of solute adsorbed per gram of formulation is also obtained for each formulation and the maximum capacity of sorbent formulation and equilibration time for each formulation is calculated. Identical experiments are performed with unencapsulated and encapsulated *E. coli* DH5 cells to determine urea utilization. Based upon the results of these experiments, five optimized mixtures of modified sorbent formulations with microencapsulated *E. coli* DH5 cells will be selected for studies in the TNO computer controlled Gastro-Intestinal track model, also referred to as the Dutch stomach model, and for studies in animals.

Example 6
TNO Gastro-Intestinal Model (TIM)

The TNO gastrointestinal model (TIM) simulates very closely the successful dynamic conditions in the lumen of the gastrointestinal track. Dynamic parameters that are simulated include: food and drink intake; the pH curves and the concentrations of enzymes and proenzymes in the stomach including saliva and small intestines including pancreatic juices; the concentration of bile in different parts of the gut; the kinetics passage of chyme through the stomach and small intestines; and the adsorption of water soluble digestive products and water. In the large intestinal model a complex high density microflora of human origin ferments the undigested food compounds in a natural colonic environment simulating pH values, absorption of water, and absorption of microbial metabolites such as short chain fatty acids and gas. Accordingly, this model is used to evaluate the fate of various formulations of compositions of the present invention in both the small and large intestines.

Example 7
In Vivo Studies

Rats weighing approximately 150±15 grams, with a degree of chronic renal failure (CRF) similar to that found in humans with end-stage renal disease approaching the initiation of dialysis are used to test the effects of orally administered microencapsulated sorbents and *E. coli* DH5 cells at removing uremic toxins that accumulate in CRF and in reducing uremic symptoms. Overall, there are 4 groups including a control group, a group with chronic renal failure and 2 groups with acute renal failure. Specifically, male rats weighing 250–300 grams, approximately 8 weeks in age, are purchased from Charles River or Harlan and housed in cages which prohibit rats from any access to their feces. Baseline measurements of standard clinical chemistries as well as measurements of compounds considered to be uremic toxins are determined for all animals. Rats are then made either acutely uremic or chronically uremic by surgical procedures.

Acute renal failure is produced by bilateral nephrectomy in accordance with procedures described by Waynforth, H. B. and Flecknell, P. A. Nephrectomy. In: Experimental and surgical techniques in the rat. 2nd ed., 1992, Academic Press (Harcourt, Brace, Jovanovich), London, pp. 29, 274–275. After surgery, rats are randomly paired into age or size matched groups and pair fed. Rats are fed by intragastric administration by a curved dosing needle. One group is treated with oral feeding of sorbents along with Kayexylate to control potassium (treated group). The other group receives Kayexylate alone for potassium control only (control group). Both groups are closely monitored for at least 7 to 10 days. If sorbents are effective, some prolongation of life will be observed in the treated groups as compared to the nontreated group.

Chronic renal failure (CRF) is produced by a 2-stage surgical procedure similar to that of the 5/6 nephrectomy model disclosed by Niwa et al. (*Miner. Electr. Metab.* 1997 23:179–184) and Einbacher and Carter (*J. Exp. Med.* 1966 123:239–250) but with some modifications found to give a more profound degree of renal failure similar to people closely approaching the need for hemodialysis. In this modified procedure, a soft plastic box is sutured around the remnant kidney to prevent excessive hypertrophy following contralateral nephrectomy. This also aids in controlling organ bleeding.

Specifically, a 2 stage approach is used. On the day of the proposed surgery, food is withheld for one hour. The animal is then anesthetized with the inhalation agent, isoflurane (FORANE). The anesthetized rat is placed on its ventral side, left to right of the surgeon. Both flanks are minimally cleaned of fur with an Oster shaver and prepped with Betadine. A sterile field is prepared on the rat's left flank. A dorsoventral incision is made into the abdomen cavity, down the side of the rat near to the costal border of the thorax on the left side. The left kidney is freed of connective tissue and is pulled out gently, preferably by grasping the perirenal fat. The adrenal gland, which is attached loosely to the anterior pole of the kidney by connective tissue and fat, is gently freed by tearing the attachments. The kidney is positioned to have both poles ligated close to the point where the renal artery enters the organ. A loose lasso of new 4.0 monofilament silk is placed around the upper pole and tied tightly taking care not to break the knot. A double reef knot is used. The organ is examined for excessive bleeding. If necessary, diathermy is used to stop oozing and oxycel is used on the cortex. The same procedure is repeated on the lower pole. The remnant kidney is encased in a pre-made plastic, preferably SARAN wrap, box and secured. The organ is then placed back into the abdomen and the incision closed in 2 layers. The area is swabbed with Betadine and the animal allowed to recover. An analgesic, buprenorphine (0.25 mg/kg) is administered to relive pain. About 3 to 4 weeks later the right kidney is removed. In this surgery, an abdominal approach is used to permit examination of the remnant kidney. The anesthesia is the same, but a midline incision is made along the linea alba, minimizing bleeding. The bowel is gently moved and the left remnant kidney observed to insure some function. Adjustments to the box are made if necessary. Assuming all is well with the left kidney, the right kidney is exposed and freed from its capsule (leaving the adrenal) and then removed by placing a ligature around the renal blood vessels. Another ligature is placed around the ureter as far from the kidney as possible, towards the midline, but without damaging or occluding any collateral blood vessels that may be encountered. The ligature is tied securely with a double reef knot, and the blood vessels are transected next to the kidney, which is then removed. The incision is closed, an analgesic is given and the animal is permitted to recover in a warm area.

Serum creatinine levels of 2.6±0.2 (range 2.3 to 3.5) and blood urea levels of 98±5 with low morbidity (less than 20% by 4 weeks post-op) have been attained consistently in rats with this modified procedure.

Approximately 5 days after the second surgery, contralateral blood is drawn and rats are matched as closely as possible for weight, serum creatinine and blood urea. They are randomly assigned into a series of 4 groups. Groups A and B are pair fed. Group A consists of CRF rats without any test sorbents. Group B rats receive sorbent. A third group, Group C, is given sorbents and allowed free access to food and water. A comparison between Groups B and C shows the effects of uremia on appetite and nutrition. A fourth, sham operated group, Group D is used as controls. Rats are observed over a 4 to 7 month period during which they have biweekly blood and urine collected and assayed for dimethyl- and/or trimethyl-amine via gas chromatography as described by Dunn et al. Analytical Chemistry 1976 48:41–44. Animals are also weighed weekly and blood pressure and urine osmalities are measured monthly. They are assessed daily for appetite by following food and water intake. Timed urine collections are also performed monthly and spot urine collected biweekly. Skinfold thickness is also assessed as an additional nutritional measurement. Rats are sacrificed at 7 months and terminal bloods are drawn for clinical chemistries as well as other specific tests. Blood, urine and brain tissue are also assayed for dimethylamine.

For these studies, sorbents are in a suspension form in sterile saline and are administered orally to the rats using a 12 gauge gastric lavage tube.

What is claimed is:

1. A microencapsulated and enteric coated composition comprising:

a) a mixture of sorbents with specific adsorption affinities for uremic toxins wherein the sorbents comprise oxystarch, locust bean gum and activated charcoal; and b) a bacteria which metabolizes urea and ammonia, wherein the microencapsulation and enteric coating protects a patient taking said composition from microbial infection by said bacteria, and wherein the enteric coating disintegrates and dissolves at or above a pH of 7.5.

2. The composition of claim 1 wherein said sorbents have specific adsorption affinities for ammonia, urea, creatinine, phenols and indoles.

3. The composition of claim 1 further comprising a phosphate binding agent.

4. The composition of claim 3 further comprising a water binding agent.

* * * * *